United States Patent
Buser et al.

(10) Patent No.: US 10,482,785 B2
(45) Date of Patent: Nov. 19, 2019

(54) MULTI-SENSOR SYSTEM AND METHOD TO DETER OBSESSIVE COMPULSIVE BEHAVIOR

(71) Applicant: Shave Away Europe, Inc., San Diego, CA (US)

(72) Inventors: John Buser, San Diego, CA (US); Randall Ewen Park, Toronto (CA)

(73) Assignee: SHAVE AWAY EUROPE, INC., San Diego, CA (US)

( * ) Notice: Subject to any disclaimer, the term of this patent is extended or adjusted under 35 U.S.C. 154(b) by 0 days.

(21) Appl. No.: 16/148,998

(22) Filed: Oct. 1, 2018

(65) Prior Publication Data

US 2019/0043384 A1 Feb. 7, 2019

Related U.S. Application Data

(63) Continuation-in-part of application No. 15/615,081, filed on Jun. 6, 2017, now abandoned.

(51) Int. Cl.
*G08B 21/00* (2006.01)
*G09B 19/00* (2006.01)
(Continued)

(52) U.S. Cl.
CPC .............. *G09B 19/00* (2013.01); *A61B 5/165* (2013.01); *A61B 5/746* (2013.01); *G01V 3/08* (2013.01); *G01V 15/00* (2013.01); *G08B 21/182* (2013.01); *A61B 5/1114* (2013.01); *A61B 5/6803* (2013.01); *A61B 5/6822* (2013.01); *A61B 5/6824* (2013.01); *A61B 5/6826* (2013.01); *A61B 2562/0257* (2013.01)

(58) Field of Classification Search
CPC ....... G09B 19/00; A61B 5/6826; A61B 5/746; A61B 5/6824; A61B 5/6822; A61B 5/165; A61B 5/6803; A61B 5/1114; A61B 2562/025; G08B 21/182; G01V 3/08; G01V 15/00
USPC .... 340/686.1, 539.15, 573.1, 539.11, 539.12
See application file for complete search history.

(56) References Cited

U.S. PATENT DOCUMENTS

| | | | | |
|---|---|---|---|---|
| 4,440,160 A | * | 4/1984 | Fischell | A61N 1/38 128/846 |
| 8,585,588 B2 | * | 11/2013 | Kovarik | A61B 5/1114 600/300 |

(Continued)

*Primary Examiner* — Anh V La
(74) *Attorney, Agent, or Firm* — Steins & Associates, P.C.

(57) ABSTRACT

A Multi-sensor System and Method to Deter Obsessive Compulsive Behavior by generating alerts when a user's hands are held close to their head or face. The system includes a sensor and a triggering device that are both worn by the user. The sensor can be configured to detect when the triggering device closes to within some threshold distance. The system includes at least two magnet-sensing sensors, and is capable of being calibrated in order to eliminate interference due to the Earth's magnetic field. The sensor and triggering device may be contained within common personal items, such as jewelry—including rings, bracelets, hair clips, necklaces and the like. The system and method can generate audible and/or visual alerts whenever one or more triggering devices passes closer to the sensor than the threshold distance. Alerts are in a variety of tones, including simulated cellular telephone ring tones. Data for alert events is downloadable from the sensor device for later review.

19 Claims, 8 Drawing Sheets

(51) Int. Cl.
*G01V 3/08* (2006.01)
*G08B 21/18* (2006.01)
*A61B 5/00* (2006.01)
*A61B 5/16* (2006.01)
*G01V 15/00* (2006.01)
*A61B 5/11* (2006.01)

(56) References Cited

U.S. PATENT DOCUMENTS

| | | | |
|---|---|---|---|
| 2002/0109596 A1* | 8/2002 | Phillips | G08B 1/08 340/573.1 |
| 2007/0080812 A1* | 4/2007 | Perlman | A61B 5/1127 340/573.1 |
| 2012/0143400 A1* | 6/2012 | Hinkel, III | B62D 1/00 701/2 |

* cited by examiner

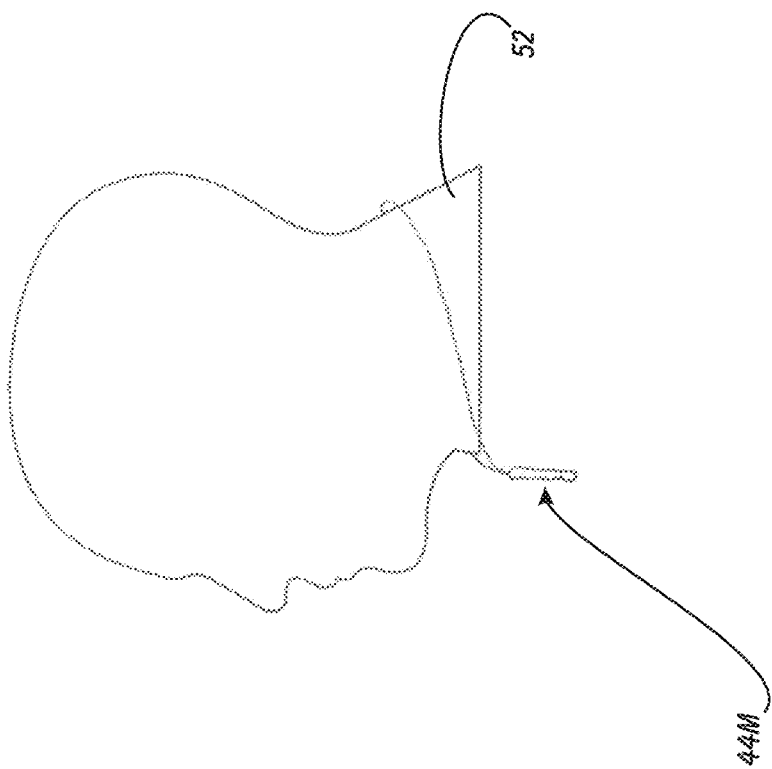
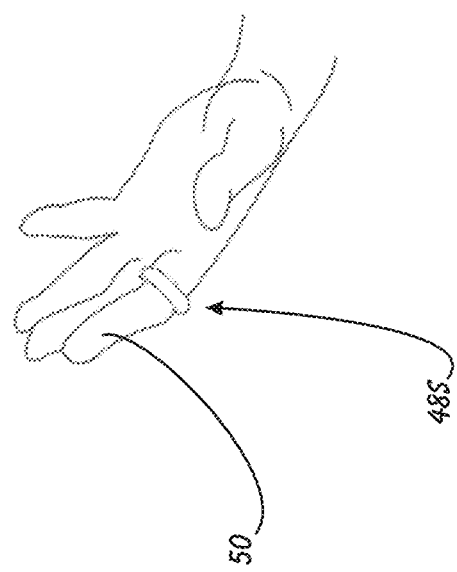
FIG. 5

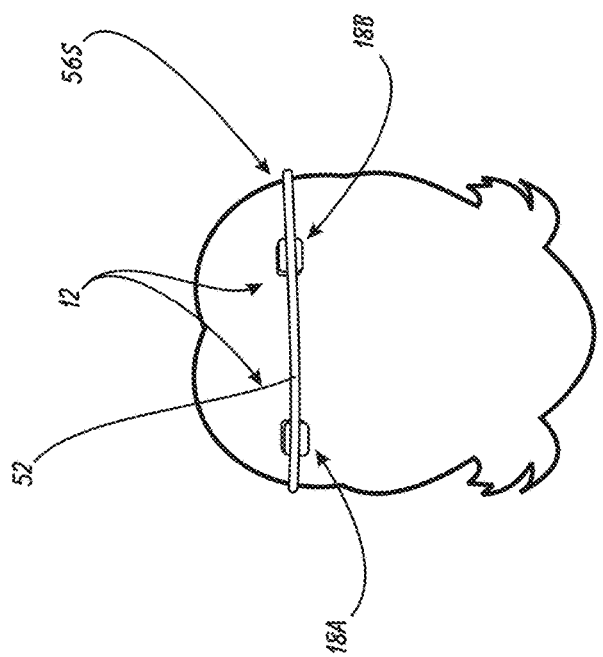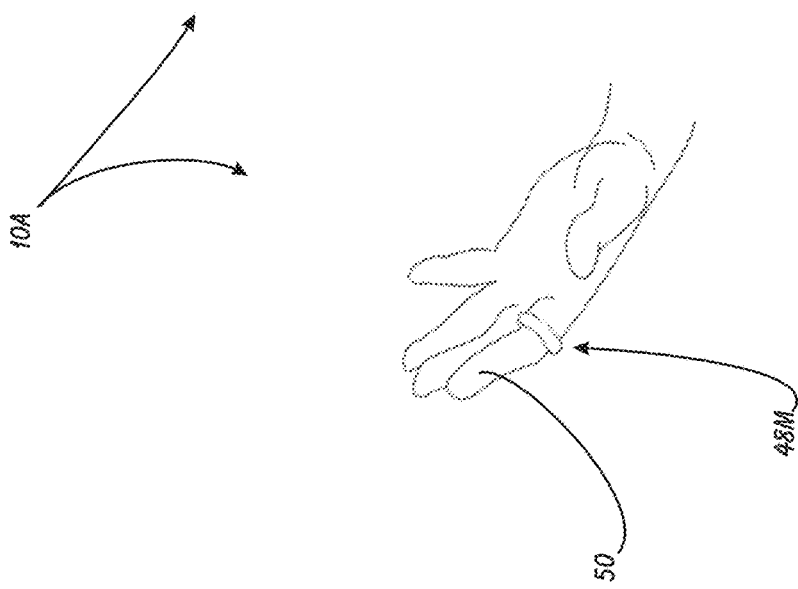
FIG. 7

MULTI-SENSOR SYSTEM AND METHOD TO DETER OBSESSIVE COMPULSIVE BEHAVIOR

This application is a Continuation-in-Part of application Ser. No. 15/615,081, filed Jun. 6, 2017; status: Pending.

BACKGROUND OF THE INVENTION

1. Field of the Invention

This invention relates generally to personal wellness systems and, more specifically, to a Multi-sensor System and Method to Deter Obsessive Compulsive Behavior.

2. Description of Related Art

Harmful personal habits can be extremely debilitating and damaging to the individuals experiencing them. Nail biting, smoking, scratching and binge eating are some of the more benign examples of these behaviors. There are also very serious psychological ailments that involve repetitive, harmful behaviors. Trichotillomania is an obsessive compulsive disorder characterized by the compulsive urge to pull out one's hair, leading to hair loss and balding, distress, and social or functional impairment[1]. This and other behaviors are very difficult to break, particularly since they usually are not noticed until such time as they have become well-seated habits.

Wikipedia: Huynh M. Gavino A C, Magid M (June 2013). "Trichotillomania". *Semin Cutan Med Surg* 32(2): 88-94.

One recently-unveiled device touts itself as being an effective tool for individuals to break bad habits—the "Pavlok" wearable device. FIG. 1 depicts this device. The Pavlok device 1 is a wrist-mounted device that provides audible alerts, vibration, and even electrical shocks to the wearer in response to pre-programmed settings (or if triggered manually). The device 1 has two main components: a wrist band 2 and a functional module 3 that inserts into a chamber formed in the wrist band 2. When intialized, the functional module 3 communicates with a personal electronic device 4 (e.g. a smart phone) via a wireless communication link 5 (e.g. bluetooth).

The functional module 3 has some spatial sensing capability, which apparently allows it to detect its orientation, and therefore the orientation of the user's wrist. This information is communicated to the electronic device 4, and a software application on the device 4 can command the functional module 3 to emit a sound, vibration or electrical shock when the module 3 returns to a pre-set location/orientation. In this way, apparently the device 1 can be programmed to shock the wearer whenever the wearer reaches his or her hand to their head, such as to pull out their hair.

The personal electronic device 4 can also be set to communicate with the world-wide web 7 via its wide-area network communications conduit (e.g. cellular connection) so that the device can be programmed to deter the wearer from visiting undesirable web sites. To activate this, the user installs an application on their computer 8 and initializes it to create a trigger if any of the user-programmed website locations. The trigger is communicated via wide area network conduits 6 through the world-wide web to the personal electronic device 4, which then commands the functional module 3 to generate an alert and/or shock to the wearer.

While the Pavlok device is likely to be a valuable tool for many circumstances, it suffers from several problems in its effectiveness because of the complexity of its design. The Pavlok system is not configured to handle more than a single functional module 3 at one time. As a result, the wearer can "fool" the device 1 by simply using their non-wrist-banded hand to engage in the harmful behavior. Second, while great functionality is achieved by its connection to the personal electronic device 4, it also creates a hindrance—the wearer must always have a smart phone or equivalent device within 30 feet of the device 1. This is not always possible, particularly when the wearer is a child (who may not have a smart phone), or when having a smartphone in such close proximity is not possible or convenient.

What is needed, therefore, is a device, system and method that does not require a smartphone or other external personal electronic device 4 in order to be active. This device should also be capable of monitoring the movements of both of the wearer's hands, and not be limited to a single hand at one time.

SUMMARY OF THE INVENTION

In light of the aforementioned problems associated with the prior devices, systems and methods, it is an object of the present invention to provide a Multi-sensor System and Method to Deter Obsessive Compulsive Behavior. The system should include a sensor and a triggering device that are both worn by the user. The sensor should be configured to detect when the triggering device closes to within some threshold distance. The system should include at least two magnet-sensing sensors, and should be capable of being calibrated in order to eliminate interference due to the Earth's magnetic field. The sensor and triggering device should be contained within common personal items, such as jewelry—including rings, bracelets, hair clips, necklaces and the like. The system and method should generate audible and/or visual alerts whenever one or more triggering devices passes closer to the sensor than the threshold distance. Alerts should be in a variety of tones, including simulated cellular telephone ring tones. Data for alert events should be downloadable from the sensor device for later review.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

FIG. 5 is a side view of an exemplary use case of the system of FIG. 1;

FIG. 7 is a side view of a third exemplary use case of said system; and

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a System and Method to Deter Obsessive Compulsive Behavior.

Figure 2:
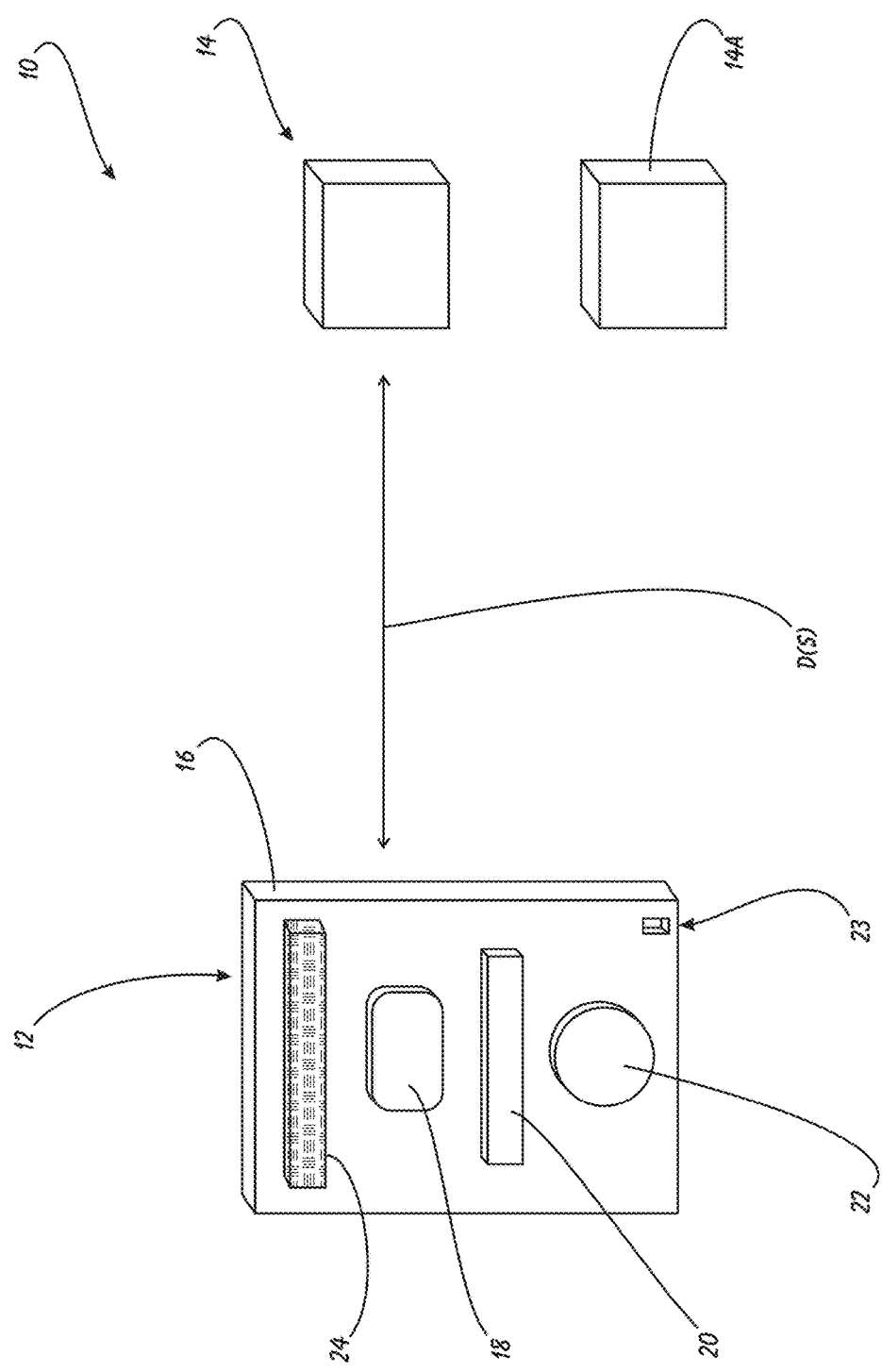
FIG. 2 is an exploded perspective view of a preferred embodiment of the proximity alert system of the present invention.

The present invention can best be understood by initial consideration of FIG. 2.[2] FIG. 2 is an exploded perspective view of a preferred embodiment of the proximity alert system 10 of the present invention. The system 10 has a sensor subassembly 12 and one or more magnet subassemblies 14, 14A (which can also be referred to as trigger subsystems 14, 14A). The subassembly 12, when configured and activated, will detect when one of the magnet subassemblies 14, 14A closes to a distance D(s) that is closer than the threshold distance (D(threshold)) that has been configured in the sensor subassembly 12. The magnet subassemblies 14, 14A are preferably made of niobium because of its inherent low toxicity and its ability to be colored by anodizing. Other rare earth magnet material might also be utilized.

As used throughout this disclosure, element numbers enclosed in square brackets [ ] indicates that the referenced element is not shown in the instant drawing figure, but rather is displayed elsewhere in another drawing figure.

The sensor subassembly 12 may be contained within a housing (not shown) that could, in some forms, be water-resistant, waterproof and/or shock-resistant. The subassembly 12 has a plurality of components mounted to a substrate 16, such as a printed circuit board. The sensor system 18 is designed to detect the proximity of the magnet subassemblies 14, 14A to the subassembly 12 (by measuring the presence of the magnetic field(s)). The sensor system 18 may also have the capability to detect its spatial orientation in order to assist in the triggering process.

Output system 24 could simply provide audible alerts, but it could also be outfitted with an internal vibration-generating device and a light source. The audio alerts should be configurable to that the user's most desirable sound is emitted—including a sound that mimics that user's cellular telephone's ringtone (in order to disguise the alert for third parties). The onboard power source 22 would typically be a rechargable battery that is recharged via plugging the subassembly 12 into an external computer or charging source at the port 23.

The control system 20, such as a microprocessor or the like, controls the features and functionality of the subassembly 12, the configuration and settings, and the handling and delivery of data, such as through the communications/charging port 23 (e.g. micro-USB for connection to an external computer or to a charging device).

In another version, the magnet subassemblies 14, 14A may be replaced with devices that utilize a different technology. For example, they may incorporate RFID chips that generate a signal for receipt by the sensor system 18 when the subassemblies 14, 14A come within D(threshold) to the sensor subassembly 12. Alternatively, Near-field communications or other technology may be employed. In any version, the key attribute is that the sensor subassembly 12 will cooperate with the subassemblies 14, 14A (magnetic or other) so that the subassembly 12 will register a trigger when D(s) is reduced to a pre-set distance. If we now turn to FIG. 3, we can examine how the system 10 operates.

Figure 1:
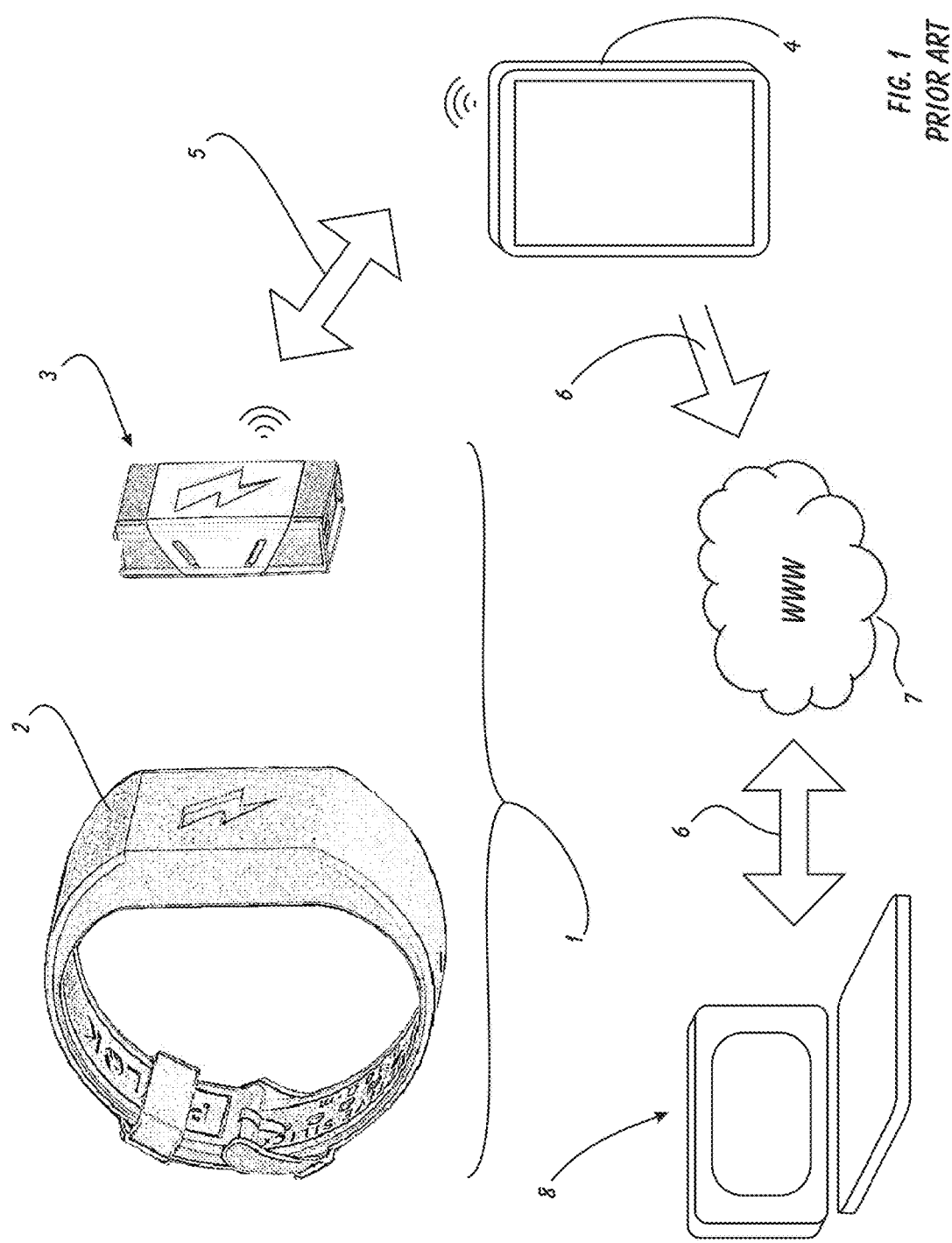
FIG. 1 is a functional diagram of the "Pavlok" device.
Figure 3:
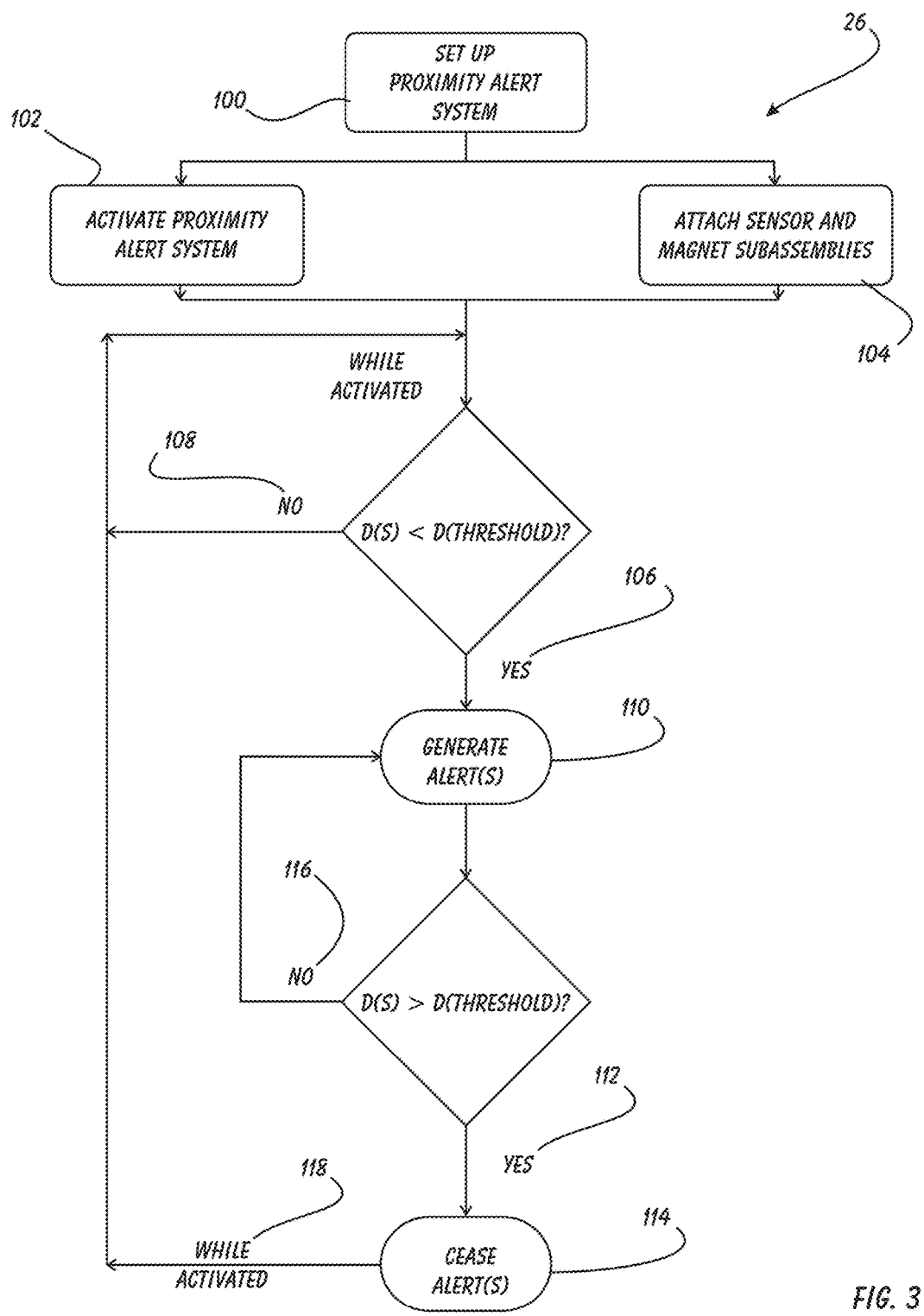
FIG. 3 is a preferred alert method of the system of FIG. 1.

FIG. 3 is a preferred alert method 26 of the system of FIG. 1. The user first sets up the proximity alert system 100. This generally entails connecting the sensor subassembly [12] to an external computing device via port [23]. The user can set alert sounds/tones/volume, vibration on/off, data logging periodicity and the sensitivity of the system (i.e. the distance and duration that D(s) must reach in order to generate an alert). Sensitivity settings are used to minimize the occurrence of false alarms. There may also be a visible alert that can be configured in this manner.

The user then activates the system 102 and attaches the sensor and magnet (or non-magnet) subassemblies to their person 104. These two steps can be done in any order that is most convenient to the user. Once activated 102, the system [10] will function automatically until deactivated—assuming that the settings are properly entered, this will interfere with the behavior being deterred before the behavior actually occurs.

Figure 4:
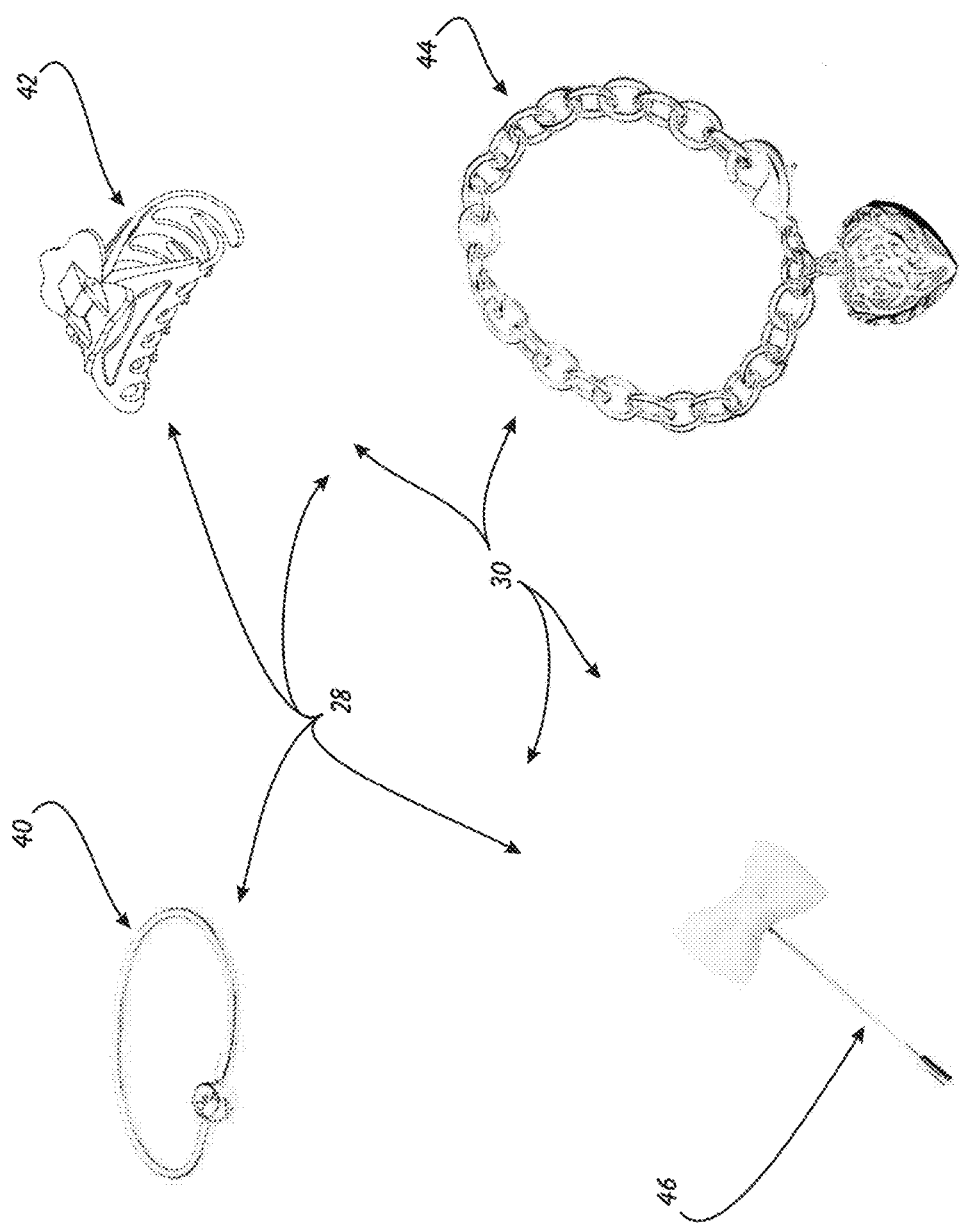
FIG. 4 is a grouping of potential embodiments of the components comprising the system of FIG. 1.

The system [10] perpetually detects whether or not D(s) is less than D(threshold) (i.e. if the magnet/trigger device is too close to the sensor subassembly [12]). In one particular exemplary system [10], D(threshold) is approximately 8 (eight) inches. As soon as the condition is met 106, the alerts will be generated 110 (as set up in step 100). If D(s) is not greater than D(threshold) 116, the alerts will continue to be generated 110. Once D(s) is greater than D(threshold) 112, the alerts will cease, and the system [10], while activated 118, will continue to monitor D(s) as it compares to D(threshold). FIG. 4 depicts several examples of possible embodiments for the devices comprising the system [10].

FIG. 4 is a grouping of potential embodiments of the components comprising the system [10] of FIG. 1. As a preliminary matter, it is the intent that "magnet assemblies" referred to herein contain triggering elements that are detected by the sensor subassembly [12] so as to determine D(s). The triggering element could be a magnet, but could also be and RFID transmitter or employ other distance-determining technology.

Figure 6:
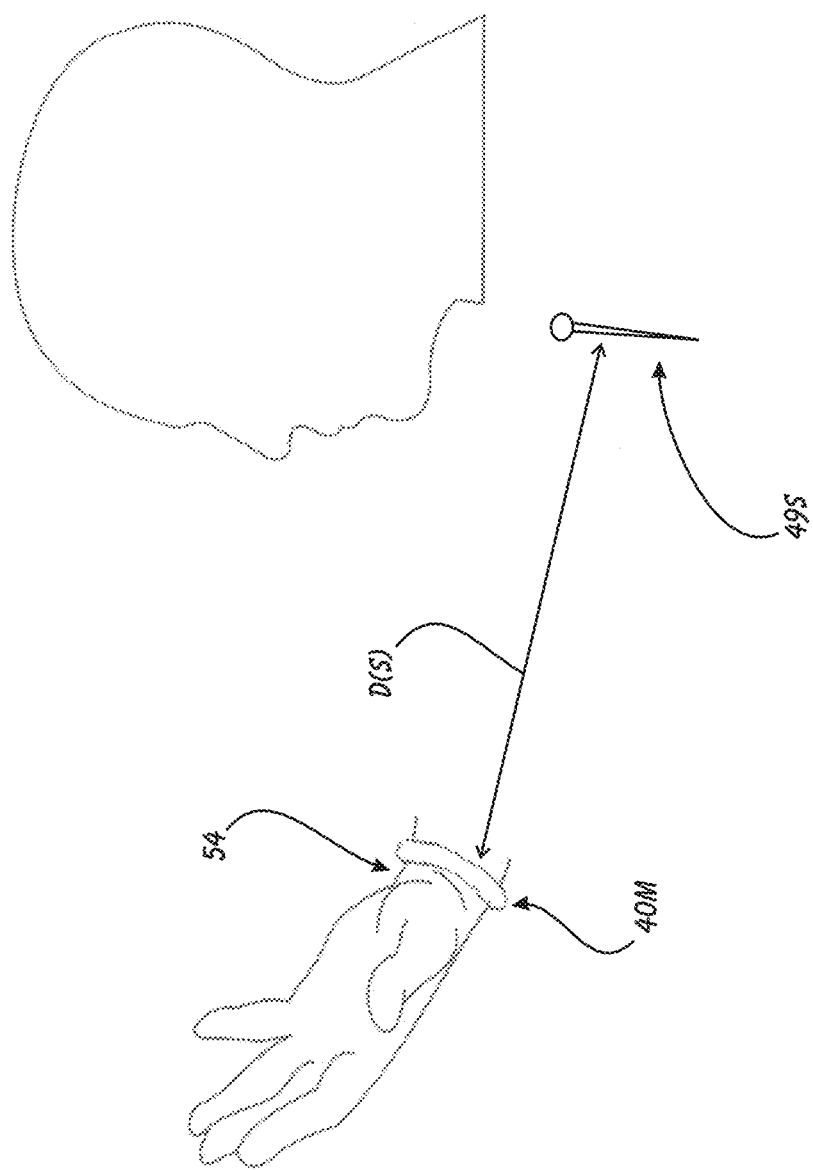
FIG. 6 is a side view of a second exemplary use case of said system.

The sensor assemblies 28 each contain a sensor subassembly [12]. The magnet assemblies 30 each contain a magnet subassembly [14]. As shown, the assemblies 28, 30 are not confined to any particular personal device. Examples here are a bracelet 40, a hair clip 42, a necklace 44 and a pin 46 (hair or lapel). The sensor subassembly [12] could be in a bracelet 40, while the magnet subassembly [14] could be in a hair clip 42 (or vice versa). The sensor subassembly [12] would then generate an alert whenever the bracelet 40 is closer than D(threshold) to the hair clip 42. FIGS. 5 and 6 depict other examples possible in this system [10].

In FIG. 5, necklace magnet assembly 44M is attached to the user's neck 52. A ring sensor assembly 48S is around the user's finger 50. As should be apparent, whenever the user's finger 50 closes within D(threshold) of the user's neck 52, and alert will be generated.

Similarly, as shown in FIG. 6, a bracelet magnet assembly 40M is being worn around the user's wrist 54, while the tie pin sensor assembly 49S is attached to the user's garment, and the alert(s) are generated when D(s) is less than D(threshold).

FIG. 7 depicts yet another arrangement of the components of the present invention. The magnet is contained within one or more ring magnet assemblies 48M worn on fingers 50 of one or both of the user's hands. In this version, the ring assemblies 48M can be small and stylish, since the magnets [14/14A] are smaller than the sensor subassembly 12.

A pair of sensor subassemblies 12 are attached to, or encased within a head band sensor assembly 56S. The first and second sensor elements 18A, 18B are in relative spaced relation in order to allow them to detect magnetic fields at different positions around the user's head. The head band 58 could be the thin, unadorned version shown here. In such a case, the user may wear the assembly 56S underneath a more decorative headband, or under a hat/cap. In other versions, the assembly 56S will be housed within a separate, decorative casing (optionally selected from a series of casings) that can be removed from the assembly 56S, such as for cleaning and/or replacing with an alternate casing.

Magnetic sensors have a lower limit on the magnitude of magnetic field they can detect. The strength of a permanent magnet's magnetic field decreases as the cube of the distance between the magnet. As such, a sensor system having a detection distance of ten inches must be eight times more sensitive than a sensor system having a detection distance of five inches. More importantly, the Earth's magnetic field is stronger than the magnetic field of a small permanent magnet a fairly small distances from the small permanent magnet. Therefore, a single magnetic field sensor would have great difficulty distinguishing between the Earth's magnetic field and the field of a small permanent magnet, such as is employed in the present invention.

Since the earth's magnetic field has components in three dimensions, if the user changes orientation with respect to the Earth's magnetic field while they are wearing the device the signal from the sensor will change. As well, the Earth's magnetic field is modified by external objects, locations within buildings, and so on. The most effective way to compensate for the changes in sensor signal because of these changes in the Earth's magnetic field as the user moves is to measure the magnetic field and remove its effects from the detected signal. In the present invention this is achieved by the use of two sensor subassemblies. In essence, absent the presence of a magnet the two sensors subassemblies should see the same magnetic field from the earth; if a magnet is nearby its presence will be indicated by a difference in the signals from the sensors subassemblies.

The problem caused by the Earth's magnetic field is further exacerbated by the fact that the Earth's magnetic field changes by geographic location. Since the system of the present invention is intended to be worn on the user's body, it is safe to assume that the user will not remain at a fixed geographical location. As the user moves normally, then, the Earth's magnetic field will change, and will introduce even more error and uncertainty into the field strength sensed by a magnetic sensor.

The solution to the problems presented by the Earth's magnetic field is solved by the exemplary system shown in FIG. 7. This system 10A uses two magnetic sensors positioned at different, complementary locations in the region of interest. For example, for trichotillomania the two sensors are located in a headband with one sensor roughly on each side of the user's head. The signals in each of three axes from the two sensors are compared, and a difference in magnetic field from one side to the other triggers an event.

Figure 8:
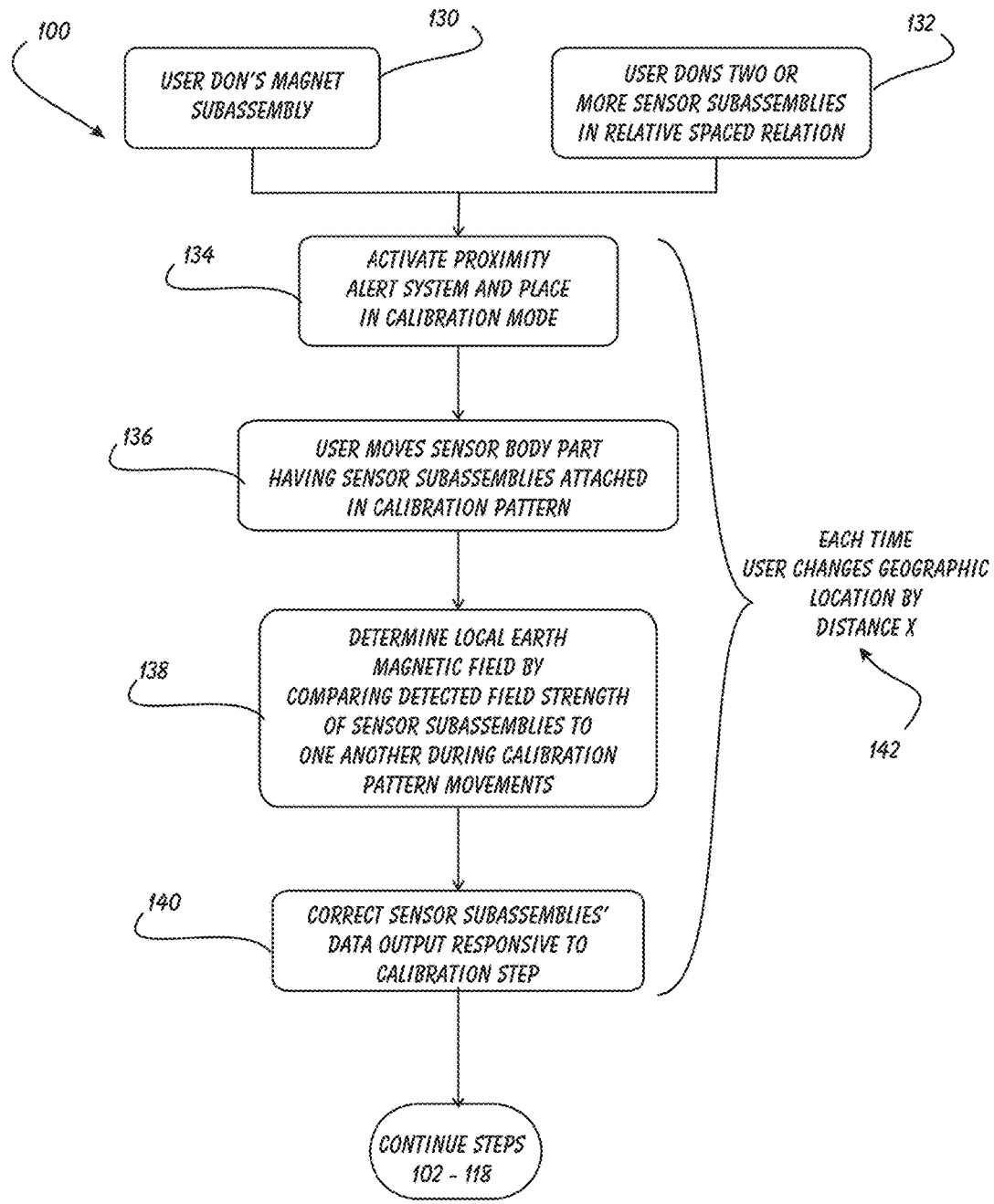
FIG. 8 is a flowchart depicting the steps of the preferred multi-sensor setup or calibration method.

FIG. 8 is a flowchart depicting the method of calibration of the multi-sensor system 10A. The method compensates for slight differences in the sensor sensitivities and imperfect sensor alignment (relative to the user's body), as well as for the local magnitude of the Earth's magnetic field.

The method 100 is referred to in FIG. 3 as the setup process for the system. First, the user dons the magnet subassembly and sensor subassemblies 130, 132. Next, the proximity alert sensor system is activated and placed in calibration mode 134. Once in calibration mode, the user is directed (either by the system, or by documentation) to move the body part to which the sensor subassemblies is attached through a series of positions 136, while the magnet is kept beyond detection distance from the sensor subassemblies.

The system will record the magnetic field detected by the individual sensor subassemblies in three axes as the user conducts the calibration movements. The system then compares the recorded magnetic field values during the calibration movements in order to determine the strength of the local earth's magnetic field 138. The system then applies a correction to the raw output of the sensor subassemblies based responsive to the strength of the local earth's magnetic field (and other sensor differences) 140.

Once the calibration method 100 is completed, steps 102-188 (depicted in FIG. 3) can be executed as desired. If the user changes their geographic location by more than distance X (which is a substantial distance), then the calibration process 100 must be executed once again.

Finally, in its typical form, the device keeps track of how often and when the behavior occurs, and stores this information. Furthermore, the user can make adjustments to the sensitivity of the sensor assembly 12, in order to prevent premature alerts (or failures to alert). Once a week when the device is charged, the information can be downloaded to the computer to monitor what situations triggered the behavior. A time and date stamp would typically be associated with each data record.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A proximity alert system to be worn by a user, the system comprising:
   at least two sensor subsystems worn on a first portion of the user's body in relative spaced relation each said sensor subsystem comprising a magnetic field detector, said sensor subsystems further comprising a calibration subsystem configured to calibrate the sensitivity of said sensor subsystems to responsively eliminate the affect of earth's magnetic field on said at least two sensor subsystems by comparing the magnetic field detected by one said sensor subsystem to the magnetic field detected by another said sensor subsystem;
   at least one trigger subsystem worn on a second portion of the user's body, said trigger subsystem including a magnetic field detectable by said sensor subsystems; and
   wherein each said sensor subsystem provides an alert perceptible to the human senses when one said trigger subsystem is placed within a threshold distance from one said sensor subsystem.

2. The system of claim 1, wherein each said sensor subsystem further comprises a substrate to which a sensor system is attached, wherein said sensor is configured to detect when the distance to any said trigger subsystem is less than or equal to said threshold distance from said sensor system.

3. The system of claim 2, wherein said sensor subsystem further comprises a control system and an output system associated with said substrate, and wherein said control system communicates with said sensor system and said output system to responsively generate output perceptible to the human senses when one said trigger subsystem is less than or equal to said threshold distance from said sensor subsystem.

4. The system of claim 3, wherein one said sensor subsystem comprises a band configured to be wrapped around the user's head.

5. The system of claim 4, wherein one said trigger subsystem comprises a ring configured to be worn on the user's finger.

6. The system of claim 5, wherein one said sensor subsystem comprises a necklace configured to be worn around the user's neck.

7. The system of claim 6, wherein one said trigger subsystem comprises a bracelet configured to be worn around the user's wrist.

8. The system of claim 3, wherein one said sensor subsystem comprises a bracelet configured to be worn around the user's wrist, and one said trigger subsystem comprises a necklace configured to be worn around the user's neck.

9. A method for providing an alert responsive to the relative proximity between one or more of a user's appendages, the method comprising the steps of:
attaching at least one sensor subsystem to a user's first appendage, each said sensor subsystem comprising at least two sensors in relative spaced relation;
moving said first appendage in a pre-determined calibration motion pattern;
adjusting the sensitivity of said sensor subsystems responsive to said moving step, such that the sensor subsystems negate the affect of the earth's magnetic field on said sensor subsystems;
attaching at least one trigger subsystem to a second appendage of the user;
monitoring the proximity of all said trigger subsystems to all said sensor subsystems; and
emitting an alert perceptible to the human senses when the distance between any said trigger subsystem is closer to any said sensor than a preset threshold distance.

10. The method of claim 9, wherein each said sensor of said sensor subsystem attaching step comprises a substrate to which a sensor system is attached, wherein said sensor is configured to detect when the distance to any said trigger subsystem is less than or equal to said threshold distance from said sensor system.

11. The method of claim 10, wherein each said sensor subsystem of said sensor subsystem attaching step further comprises a control system and an output system associated with said substrate, and wherein said control system communicates with said sensors and said output system to responsively generate output perceptible to the human senses when one said trigger subsystem is less than or equal to said threshold distance from said sensor subsystem.

12. The method of claim 11, wherein each said sensor subsystem of said sensor subsystem attaching step comprises a band configured to be wrapped around the user's head.

13. The method of claim 12, wherein each said trigger subsystem of said trigger subsystem attaching step comprises a ring configured to be worn on the user's finger.

14. The method of claim 11, wherein each said sensor subsystem of said sensor subsystem attaching step comprises a necklace configured to be worn around the user's neck.

15. The method of claim 14, wherein each said trigger subsystem of said trigger subsystem attaching step comprises a bracelet configured to be worn around the user's wrist.

16. The method of claim 11, wherein each said sensor subsystem of said sensor subsystem attaching step comprises a bracelet configured to be worn around the user's wrist, and one said trigger subsystem of said trigger subsystem attaching step comprises a necklace configured to be worn around the user's neck.

17. A wearable proximity alert system, comprising:
at least one magnet subsystem configured to be worn by a user on a first portion of the user's body; and
at least one sensor subsystem configured to be worn by the user on a second portion of said user's body, with each said sensor subsystem in spaced relation to other said sensor subsystems worn by the user, each said sensor subsystem comprising:
at least two sensor systems in relative spaced relation for detecting when one said magnet subsystem is less than a threshold distance from said sensor system;
a calibration system for comparing the magnetic field detected by one said sensor system and the magnetic field detected by the other said sensor system; and
an output system for generating an alert perceptible to the human senses when one said sensor system detects a magnetic field that is stronger than a threshold strength and also stronger than a magnetic field detected by another said sensor system.

18. The system of claim 17, wherein said sensor subsystem comprises:
a headband configured to attach around the user's head; and
said sensor system comprises a pair of sensor elements attached to said headband, wherein each said sensor element detects when any of said magnet subsystems are less than or equal to the threshold distance from said sensor element, such that the magnetic field detected by one said sensor element is above a threshold strength.

19. The system of claim 18, wherein said sensor subsystem further comprises a control system, said control system providing the user with the ability to adjust said threshold distance and said threshold magnetic field strength.

* * * * *